United States Patent [19]

Stoop et al.

[11] Patent Number: 5,144,950
[45] Date of Patent: Sep. 8, 1992

[54] RATE CONTROLLED PACEMAKER SYSTEM USING AR INTERVAL FOR RATE CONTROL

[75] Inventors: G. A. P. Stoop, Dieren; Malcolm J. S. Begemann, Velp, both of Netherlands

[73] Assignee: Vitatron Medical B.V., Dieren, Netherlands

[21] Appl. No.: 575,238

[22] Filed: Aug. 30, 1990

[51] Int. Cl.$^5$ .............................................. A61N 1/368
[52] U.S. Cl. ................................................ 128/419 PG
[58] Field of Search .................................. 128/419 PG

[56] References Cited

U.S. PATENT DOCUMENTS

| | | | |
|---|---|---|---|
| 3,903,897 | 9/1975 | Woollons et al. | 128/419 P |
| 4,284,082 | 8/1981 | Funke et al. | 128/419 PG |
| 4,387,717 | 6/1983 | Brownlee et al. | 128/419 PG |
| 4,527,568 | 7/1985 | Rickards | 128/419 PG |
| 4,535,776 | 8/1985 | Strandberg et al. | 128/419 PG |
| 4,644,954 | 2/1987 | Wittkampf et al. | 128/419 PG |
| 4,712,555 | 12/1987 | Thornander et al. | 128/419 PG |
| 4,799,486 | 1/1989 | DuFault | 128/419 PG |
| 4,856,521 | 8/1989 | Irnich | 128/419 PG |
| 4,856,524 | 8/1989 | Baker, Jr. | 128/419 PG |
| 4,972,834 | 11/1990 | Begemann et al. | 128/419 PG |

Primary Examiner—William E. Kamm
Assistant Examiner—Kennedy J. Schaetzle
Attorney, Agent, or Firm—Woodcock Washburn Kurtz Mackiewicz & Norris

[57] ABSTRACT

A pacing system and method for delivering atrial stimulus pulses is provided, wherein detected AV interval is utilized for increasing or decreasing atrial pacing interval. The AV interval is compared with an AV reference value each cycle to determine direction of change of pacing, the AV reference being updated each cycle in accordance with a predetermined correlation of change of pacing interval and change of AV reference. The pacing system may be either DDDR or AAIR. In the AAIR embodiment, a single atrial lead is used and the far field ventricular R wave signal is sensed from the total electrocardiogram signal obtained from the atrial lead.

19 Claims, 5 Drawing Sheets

RATE CONTROLLED PACEMAKER SYSTEM USING AR INTERVAL FOR RATE CONTROL

BACKGROUND OF THE INVENTION

Field of the Invention

The subject invention relates to cardiac pacemaker systems, and, more particularly, implantable cardiac pacemakers which deliver atrial pacing pulses at an adjustable rate based upon monitoring of patient conditions.

Description of the Background and Prior Art

Rate responsive pacemaker systems are widely available in the art. Rate responsive systems contain means for monitoring at least one patient variable and for determining an indicated pacing rate as a function of such sensed pacing variable, so as to control pacing rate optimally in terms of the patient condition. Such rate responsive pacemakers have gained wide acceptance as providing an improved response to the patient's physiological needs, as compared to programmable fixed rate pacemakers. Although atrial-based pacemakers, i.e. atrial synchronous or atrial sequential pacemakers, as well as DDD pacemakers, may in some patients provide an ideal form of rate responsiveness, such pacemakers are not satisfactory for many patients with cardiac conditions.

A physiological parameter which has been utilized for rate control by the assignee of this invention is the QT interval, as disclosed in the Rickards U.S. Pat. No. 4,228,803 and the Wittkampf et al, U.S. Pat. No. 4,305,396. The QT interval is in fact the interval between a delivered pacing stimulus and a subsequent evoked T-wave, and has been utilized as a parameter indicative of physiological demand for heart output, and thus pacing rate. The use of QT interval as a control parameter in a single chamber pacing system has the advantage that no additional sensor, or external connecting lead, is required, since the ventricular electrode is utilized for obtaining the QT information. However, in a DDD pacing system where it is desired to operate in an atrial stimulus mode with spontaneous conduction to the ventricle, or an AAI pacing system, the evoked QT interval is not available. It would be desirable to have a DDDR pacing system or an AAIR pacing system, which does not need an additional sensor, but which can rely on the pacing lead or leads utilized to deliver the stimulus signals. Because of this, utilization of the AV interval (more accurately the AR interval between a delivered atrial stimulus pulse or sensed P-wave, and sensed QRS ventricular depolarization) is a candidate control parameter.

In a conventional DDD pacing system, leads are inserted into both the atrial and ventricular chambers, such that a means for timing out the AV interval is present. However, for a single chamber AAI pacer, only an atrial lead is utilized, leaving the problem of determining the timing of the R signal in relation to the delivered atrial stimulus. Applicants have overcome that problem, by determining that the ventricular depolarization, or V signal, can be sensed by an atrial electrode, i.e. the far field ventricular R wave signal can be separated out timewise and accurately sensed. The ability to use the AV interval as a rate indicator in a single lead AAI pacemaker is based upon accurate detection of the far field ventricular deflection portion of the signal sensed in the atrium.

SUMMARY OF THE INVENTION

It is an object of the invention to provide a pacing system and method for DDDAR or AAIAR pacing, whereby the atrial stimulus rate is controlled as a function of sensed AR time interval based on an algorithm which adjusts each pacing cycle in accordance with a reference AV interval against which the measured AR interval is compared, thereby to adjust atrial pacing rate optimally in view of the patient's heartbeat characteristics.

It is a further object of this invention to provide an AAIR pacing system and method wherein the atrial stimulus rate is responsive to sensed AR time interval, the system having a single atrial lead and related processing means for sensing both atrial and ventricular signals and for deriving the AR interval therefrom.

In accordance with the above objectives, there is provided a pacing system for delivering atrial stimulus pulses, having means for determining the patient AV interval and increasing or decreasing pacing interval as a function of such determination. The AV interval is compared with a reference in order to determine direction of change of pacing rate, the reference being updated each pacing cycle in accordance with a predetermined correlation between change of pacing interval and change of AV reference. The system also makes provision for adjusting the AV reference, and thus the pacing rate, to shift rate control at upper rate limit and lower rate limit in a manner to bring the AV reference into line with sensed AV time interval, thereby adapting the pacer response to patient conditions. In a preferred embodiment an AAIR pacing system and method are provided for sensing the far field ventricular R wave signal from the atrial electrode that delivers the atrial stimulus pulses, thereby providing single chamber atrial pacing utilizing a single atrial lead.

DESCRIPTION OF THE PREFERRED EMBODIMENTS

As used in this specification, the following abbreviations and symbols are used, as defined herein:

| Symbol | Definition |
| --- | --- |
| A | Atrium or atrial |
| AR | Interval between A pace and V sense (ms) |
| AV | Interval between A event and V event (ms); note that AV = AR when a V sense follows an A pace |
| $AV_{ref}$ | Reference value of AV interval (ms) |
| Delta | Incremental change in $AV_{ref}$ (positive or negative) accompanying change in pacing interval (ms) |
| Drift | Change, or drift introduced to $AV_{ref}$ (suitably 100 ms) at URL or LRL, or to override natural atrial signal |
| DDDAR | DDD pacer (dual chamber) with atrial rate responsive to AR interval |
| AAIAR | AAI pacer with atrial rate responsive to AR interval |
| RP | Reference point ($AV_{ref}$, $T_{rr}$) |
| $T_{aai}$ | Atrial pacing escape interval (ms) |
| $T_{rr}$ | Calculated atrial pacing interval (ms) |
| $T_{rr'}$ | Adjusted atrial pacing interval (ms) |
| lrl | Pacing interval at Lower Rate Limit (ms) |
| LRL | Lower Rate Limit (stimulus pulses per minute) |
| url | Pacing interval at Upper Rate Limit (ms) |
| URL | Upper Rate Limit (stimulus pulses per minute) |
| V | Ventricle, or ventricular |
| $V_{stim}$ | Ventricular stimulus pulse |

In the discussion below, AV is used substantially interchangeably with AR. Thus, reference is frequently made to the AV interval and $AV_{ref}$ in a context where it is clear that AR interval could be referred to.

Our investigations have indicated that a substantially linear relation exists between the workload of a patient and the patient AR interval, whereby for a given atrial pacing rate the AR interval decreases when workload increases. At the same time, a relation has been found between the pacing rate and the AR interval whereby for a constant workload, the AR interval increases with increasing pacing rate.

Figure 1:
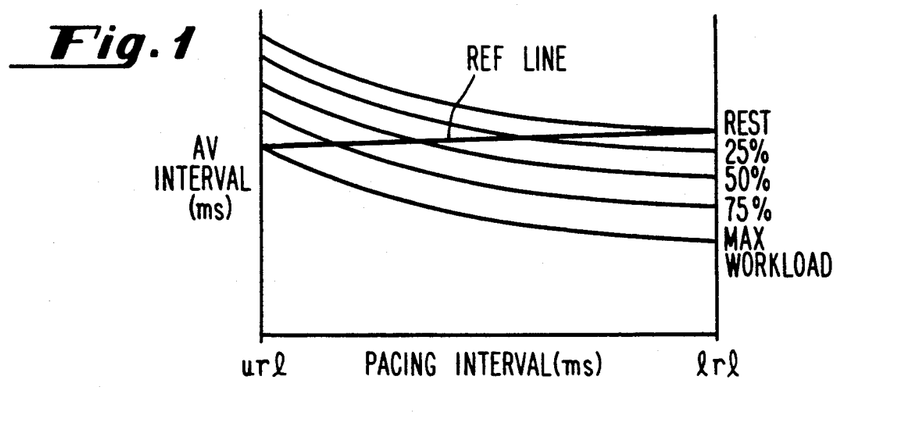
FIG. 1 presents a graph showing a plurality of patient heart curves correlating pacing interval and AV interval for respective different workload conditions, having superimposed thereon a reference line correlating the pacemaker working relationship between AV interval and pacing interval.

Referring to FIG. 1, patient heart curves are illustrated which show the variation of AV interval with pacing interval for five different workload values. A reference line is shown superimposed over the heart curves, which as illustrated provides a linear relationship between the pacing interval and changes of the AV interval. This reference line, or working line, is used in the algorithm of this invention, to link pacing intervals and AV intervals. Note that it extends from zero workload at LRL, to maximum workload at URL. The AV interval which corresponds with a certain pacing interval is the $AV_{ref}$ value; at each beat the AV interval is measured and compared with the $AV_{ref}$ interval which corresponds to the just completed actual pacing interval. It is to be noted that the invention is illustrated by a linear relationship, which provides a constant slope or correlation between change in pacing interval and change in $AV_{ref}$. However, the reference line need not be linear, and optimum results can be obtained for any given patient by adopting a non-linear reference curve to the patient heartbeat curves. The pacing system may preferably respond with larger incremental steps at lower pacing rates, than at higher pacing rates which yields a non-linear reference curve. It is also to be noted that even for a linear reference curve the slope may be positive (as shown), negative or in fact zero. If the slope is zero, $AV_{ref}$ is a constant, and pacing rate is changed in a direction to make the patient AV move toward $AV_{ref}$.

Figure 2:
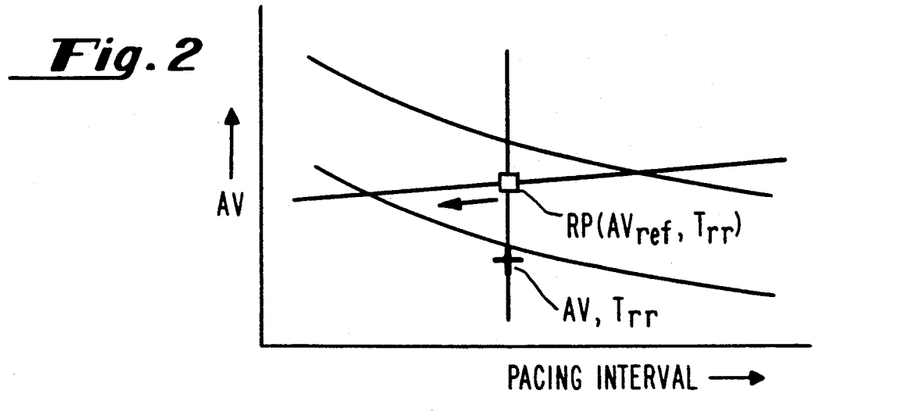
FIG. 2 is a set of curves illustrating the increase of pacing rate under conditions when the measured AV interval is found to be less than the AV reference.

Referring now to FIG. 2, the principle of the algorithm of this invention is illustrated in a situation where pacing rate is increased due to a sensed shortening of the AV interval. As illustrated, the reference point RP is the point on the reference line established during the last pacing cycle. The measured value of AV is seen to be less than $AV_{ref}$, signaling a decrease in interval (in accordance with the arrow) and a corresponding increase in pacing rate. Thus, as illustrated, a sensed shortening of the AV interval results in a pacing system response with an increased atrial stimulus rate. In the preferred software embodiment of the algorithm, as set forth in FIG. 7, when the measured AV is shorter than $AV_{ref}$, the pacing interval is decreased 12.8 ms and the $AV_{ref}$ is also decreased one step. The relation between the changes of pacing interval and $AV_{ref}$ result from a programmed slope in the reference line. Of course, if the slope is zero, there is no change in the $AV_{ref}$, but only a change in the pacing interval $T_{rr}$.

Figure 3:
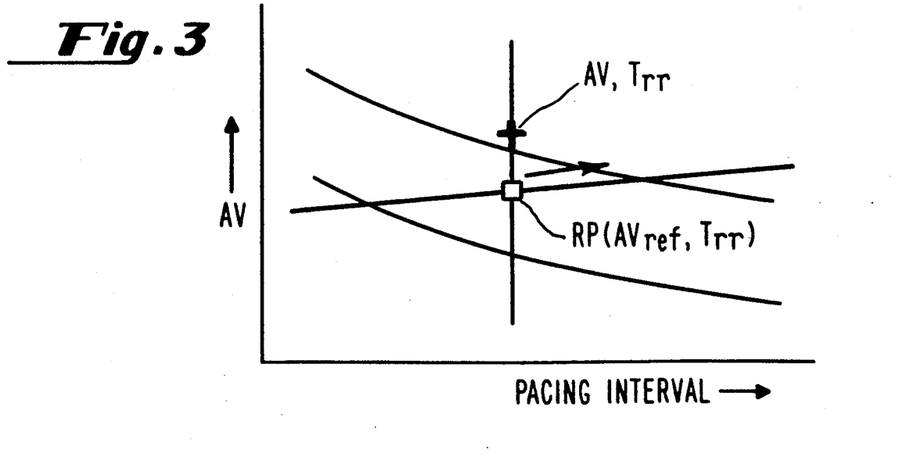
FIG. 3 presents curves illustrating a pacing system response to decreased pacing rate when measured AV interval is found to be greater than the AV reference.

Referring now to FIG. 3, the curves illustrate a decrease in the pacing rate (increase in pacing interval) when an increase in AV interval is sensed. In the situation illustrated in FIG. 3, the pacing interval is increased 12.8 ms and the AR reference interval is increased by the same increment as it is decreased corresponding to a shortening of the AV interval. Thus, as illustrated, for situations where a pacing rate is between LRL and URL, the pacing interval is adapted by increasing it or decreasing it by a fixed amount, e.g., by 12.8 ms; and the value of $AR_{ref}$ is changed according to the slope of the reference curve. If the measured AR is less than $AR_{ref}$, then the pacing interval is decreased. The $AR_{ref}$ can either be increased or decreased, or remain unchanged, depending upon the slope (positive, zero or negative). Thus, the change in $AR_{ref}$ can be toward the measured AR interval or away from it, depending on the slope.

Figure 4:
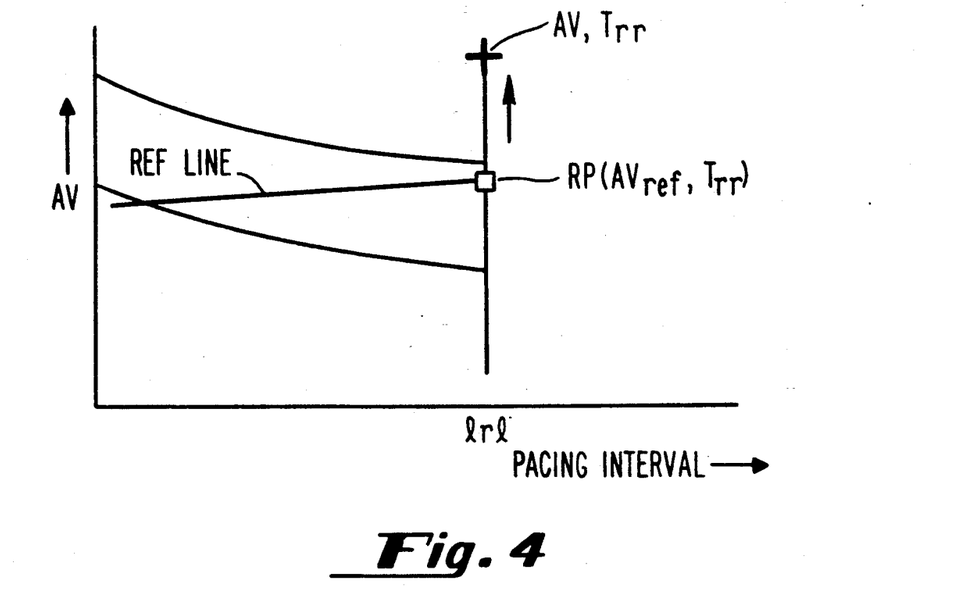
FIG. 4 presents curves illustrating adjustment of the AV reference when the pacing system is operating at lower rate limit.
Figure 5:
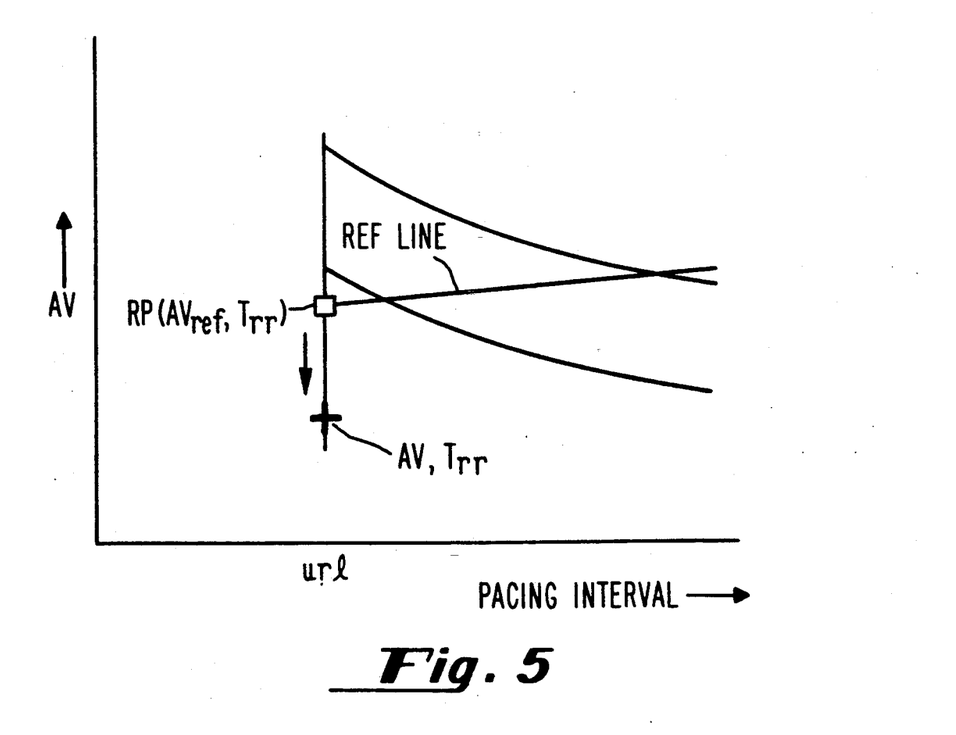
FIG. 5 presents curves illustrating adjustment of the AV reference interval when the pacing system is operating at upper rate limit.

Throughout the pacing range between URL and LRL, the pacing interval and the $AV_{ref}$ interval are continuously coupled. However, if operation of the pacing system takes the rate to either upper or lower limit, then there is decoupling of the pacing interval and the $AV_{ref}$ interval, effected by a change in the $AV_{ref}$ value only. Thus, as seen in FIG. 4, at the lower rate limit, corresponding to an interval lrl, when and if the AV interval is found to be greater than $AV_{ref}$ at the reference point, $AV_{ref}$ is incremented by a predetermined factor referred to as drift. This effectively shifts the entire reference line vertically. Correspondingly, the situation is shown in FIG. 5 where pacing rate has increased to URL and the pacing interval is stopped at url. In this situation, if the patient AV is found on a subsequent pacing cycle to be less than the value of $AV_{ref}$ at the reference point (RP) corresponding to url, then $AV_{ref}$ is decremented by a drift increment, effectively shifting the reference line downward, but not changing the slope of the line. The steps in the software algorithm of the preferred embodiment are set forth in detail in FIG. 7.

Figure 6A:
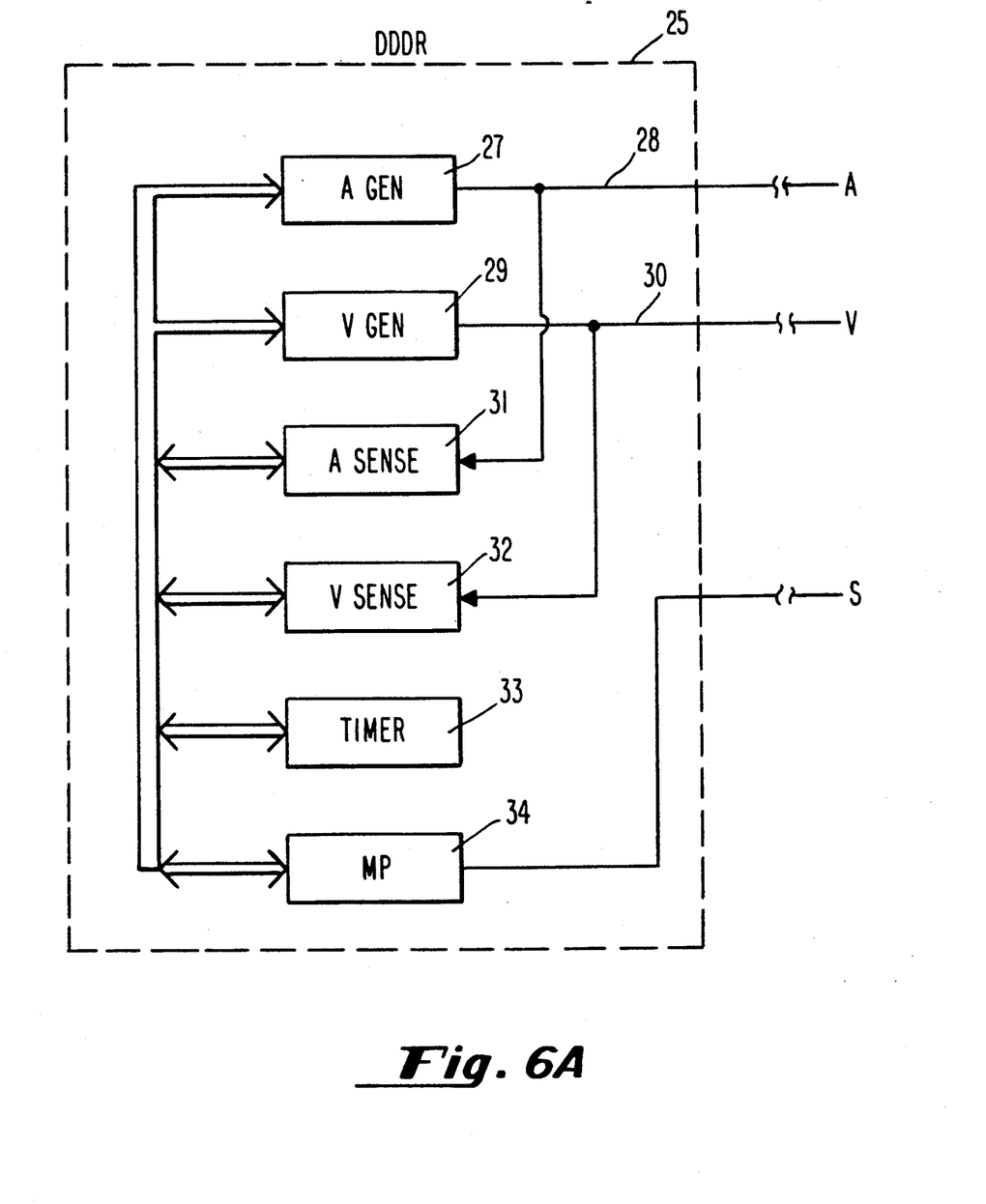
FIG. 6A is a block diagram of a DDDR pacing system in accordance with this invention.
Figure 6B:
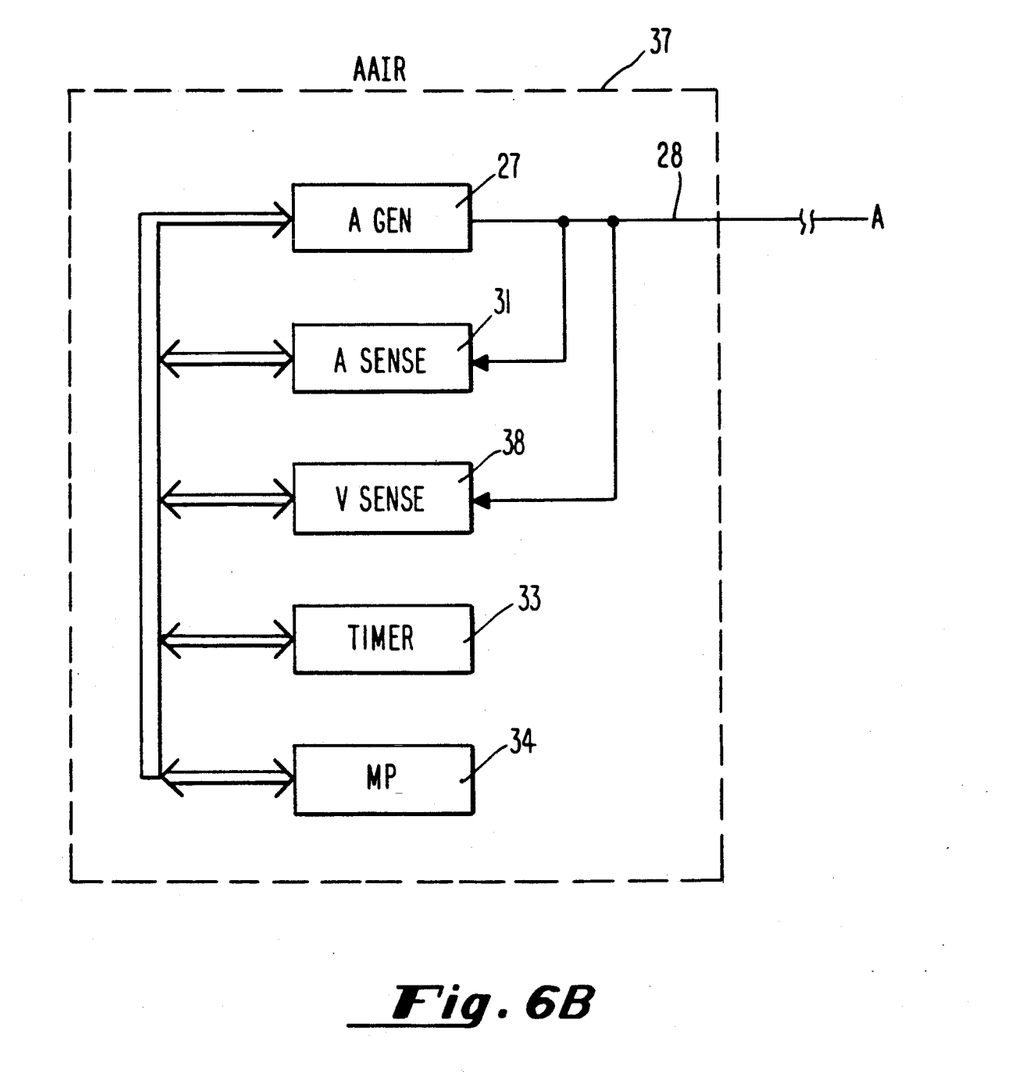
FIG. 6B is a block diagram of an AAIR pacing system in accordance with this invention.

Referring now to FIGS. 6A and 6B, there are shown block diagrams illustrative of DDDR and AAIR versions respectively of this invention. It is to be understood that the system of this invention may be utilized in either the dual chamber or single chamber embodiment, and in either case may be in communication with an external programmer (not shown) in a manner well known in the pacemaker industry. The hardware and software elements represented by FIGS. 6A and 6B are well known in the art, as are the techniques of timing out intervals and microprocessor control of pacing functions.

Referring to FIG. 6A, there is illustrated an implantable pacer at 25, having connected to it an external lead 28 having at least one electrode at about its distal tip adapted to be implanted in the patient's atrium A. It also is connected to an external electrode 30 having at least one electrode at about the distal tip thereof adapted to be implanted in the patient's ventricle. It is to be understood that the system and method of this invention may be practiced using either unilateral or bilateral leads. As shown, an atrial generator 27 is provided for generating atrial stimulus signals, the output of which is connected to lead 28. A ventricular generator 29 for generating ventricular stimulus pulses is connected to lead 30. Lead 28 is also connected to A sense circuitry 31, while lead 30 is connected to V sense circuitry 32. The A sense circuitry senses atrial heartbeats and may be used to operate the atrial channel in a demand mode. Likewise the V sense circuitry senses the occurrences of natural ventricular responses, or heartbeats, in a well known manner. Timer circuitry 33 is suitably used for timing out calculated atrial stimulating intervals, ventricular stimulating intervals, AV intervals, and the like, in a well known fashion. Timer 33 is shown controlled by logic such as that illustrated by a microprocessor ($\mu$p) at 34. Timing signals are suitably generated under control of microprocessor 34 to provide sense windows to control the sensing of the atrial and ventricular signals at circuits 31 and 32 respectively, in a well known manner. Logic under the control of microprocessor 34 also controls the timing of delivery of atrial pulses from generator 27 and ventricular pulses from generator 28.

Referring to FIG. 6B, there is shown an AAIR version of the pacing system of this invention. For such a single chamber pacing system, there is no V generator 28 or V sense circuitry 32. However, there is illustrated V sense circuitry 38, adapted to sense the far field ventricular signal (R wave) as discussed hereinabove. V sense circuitry 38 may in fact be the same sensing hardware as A sense circuitry 31, controlled by different window signals generated by timer 33 and microprocessor 34. V sense circuitry 38 comprises conventional hardware having a time response adapted to the known morphology, amplitude and slew rate of the far field ventricular signal sensed by atrial lead 28. For example, by way of illustration, the first negative ventricular deflections from the sensed far field signal are expected to have a mean of 1.42 mV; a mean duration of 28.9 ms, and a slew rate of 0.05 V/sec.

Figure 7:
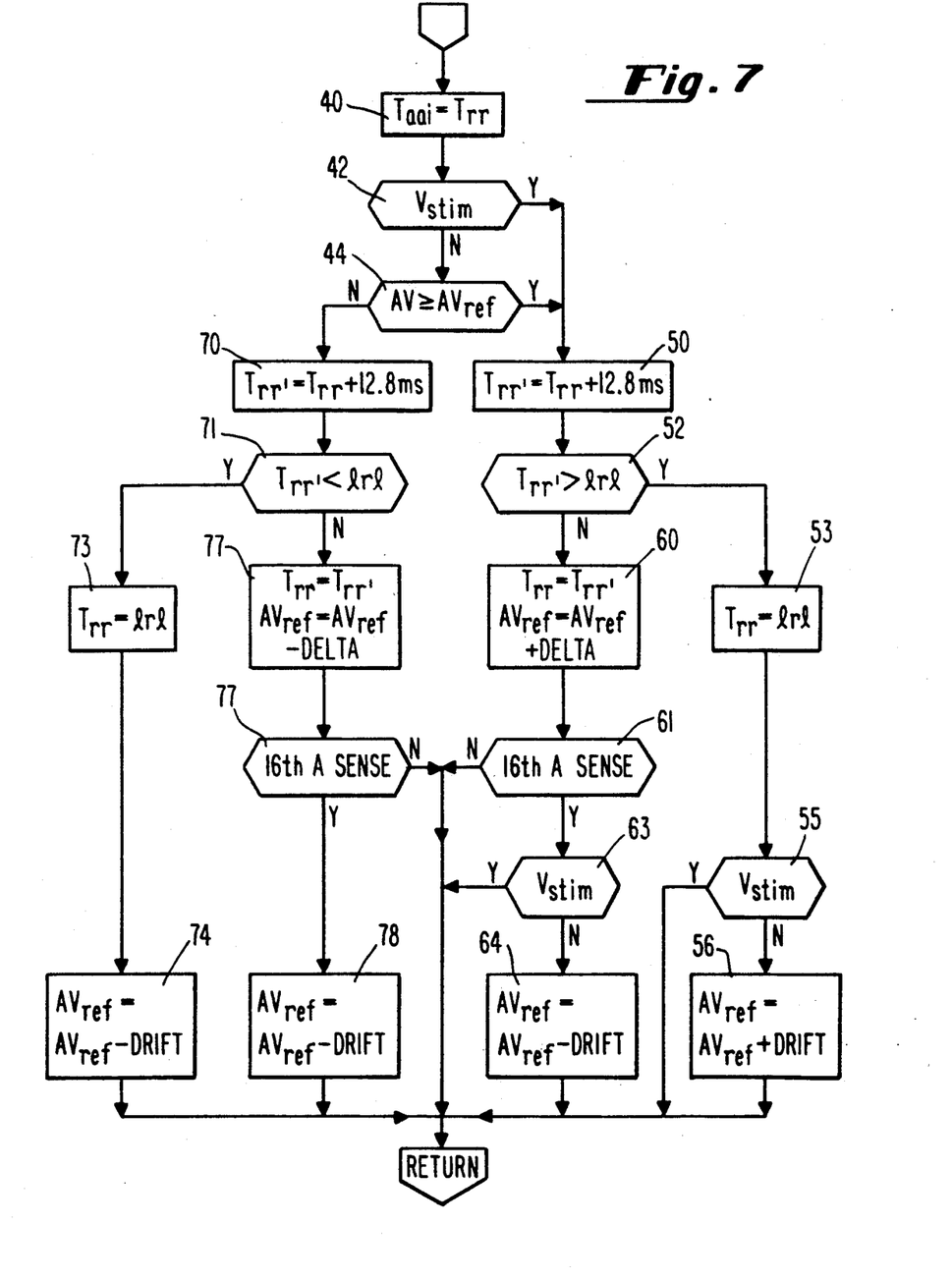
FIG. 7 is a software flow diagram illustrating a method of controlling atrial pacing rate as a function of AV interval.

Referring now to FIG. 7, the pacemaker first sets the atrial escape interval $T_{aai}$ to the calculated interval $T_{rr}$, thus establishing atrial pacing rate. Following time out of the atrial interval and the occurrence of a ventricular event, at 42 the pacer determines whether a stimulus pulse has been delivered. If no, meaning that the natural QRS was sensed, the pacer goes to block 44 in the program. If yes, meaning that no QRS was sensed during the time out of the AV interval, the program branches to block 50. At block 50, a new calculated pacing interval $T_{rr'}$ is computed equal to the prior interval ($T_{rr}$) incremented by 12.8 ms. This increment in pacing interval, which results in a decrease of rate, is performed because of the recognition that the information from the patient's heart concerning AV interval is not present. Under these circumstances, the pacer takes the atrial stimulus rate toward the lower rate limit, by adding a predetermined increment to the interval. At 52, it is determined whether the new interval is greater than lrl. If yes, the program branches to block 53 where the pacing interval is set equal to lrl. For the case where the ventricular event was a stimulus, the program branches to exit at 55. If, at block 52, the newly computed interval $T_{rr'}$ is not greater than lrl, meaning that the corresponding rate is within the permitted range between URL and LRL, the program goes to block 60 where the new pacing interval $T_{rr}$ is set equal to $T_{rr'}$. At the same time, the $AV_{ref}$ is incremented by adding a predetermined amount referred to as delta, corresponding to the slope of the reference line. The value of delta is programmable. As shown at block 63, where the last ventricular event was a V stimulus pulse, the program then exits.

Referring back to block 42, if the last ventricular event was a sensed QRS, the program goes to 44 where it is determined whether the measured AV interval is greater than or equal to $AV_{ref}$. If yes, reflecting an increase in AV, the program branches to block 50 where pacing interval is incremented. See the illustration of FIG. 3. A drift factor will be added at block 56 or subtracted at block 64, depending upon whether the newly computed pacing interval $T_{rr'}$ has increased beyond lrl. If it has, then the program shifts the reference line upward by adding a drift increment at 56, to couple pacing at LRL to the actual AV delay of the patient. See the illustration of FIG. 4. If $T_{rr'}$ is less than lrl, the program continues to block 60, as above. At 61 it is determined whether sixteen consecutive natural atrial beats have been sensed. If the answer is no, the program branches. However, if the answer is yes, then $AV_{ref}$ is decremented by drift at 64. This drift figure is introduced to increase the internal pacing rate in order to override the heart's intrinsic rate, i.e, the pacer drifts toward a rate at which an atrial stimulus ($A_{stim}$) results. This overriding is done in order that the pacemaker can update AV information such that when atrial stimulus signals have to be delivered, they are done so at approximately the desired pacing rate.

Referring again to 44, if the comparison of AV and $AV_{ref}$ indicates that AV is less than $AV_{ref}$, then the pacing system wants to increase rate, i.e. move down the reference curve toward URL, as illustrated in FIG. 2. At block 70, a new interval $T_{rr'}$, is calculated by subtracting 12.8 ms. At 71, it is determined whether this calculation results in an interval which is less than url. If yes, which is a prohibited situation, then $T_{rr}$ is set equal to url at block 73. Following this, $AV_{ref}$ is adjusted by subtracting the drift amount (suitably 100 ms) in order to adjust the reference curve toward the patient's actual AV value at URL. See the illustration of FIG. 5.

Returning to block 71, if the newly calculated pacing interval is not less than url, and thus is within the predetermined pacing range, the interval $T_{rr}$ is adjusted at 76 by setting it equal to the calculated $T_{rr'}$. At the same time, the new $AV_{ref}$ point is calculated by subtracting the predetermined amount delta from the prior $AV_{ref}$.

At 77, the determination is made as to whether there have been sixteen consecutive A sense signals. If yes, meaning that overdrive is desired, $AV_{ref}$ is decremented by the drift constant at 78, which biases the atrial pacing rate toward a higher rate.

Summarizing the operation of the algorithm, for normal operation between LRL and URL, if AV is determined to be greater than $AV_{ref}$, the pacing system adapts by incrementing the pacing interval one step (reducing rate) and adapting $AV_{ref}$ according to the slope programmed in the system. If AV interval is less than $AV_{ref}$, then the pacing interval is decreased one step (increasing rate) and $AV_{ref}$ is adapted downward according to the slope. At URL, the pacer drifts toward the measured AR interval by decrementing $AV_{ref}$ by the drift increment. At LRL, for the case of no V stimulus, the pacer drifts toward the measured AR interval by increasing $AV_{ref}$ by the drift increment. Likewise, if a V stimulus has been delivered at any point within the LRL to URL range, then there is no drift. If there have been a predetermined number of consecutive atrial senses, e.g. sixteen, $AV_{ref}$ is decremented one drift increment in order to increase pacing rate. Note that an AV interval reading also occurs after sensed atrial beats. The AV interval is then expected to be shorter than the AV interval after an atrial pacing event. This induces a kind of hysteresis. If there are sensed atrial beats, the rate will tend to increase, but when pacing takes over, the rate will tend to decrease. This effect is countered by introducing an offset in $AR_{ref}$ for sensed beats. However, whenever a V stimulus has been delivered, indicating loss of R wave, the reference position is frozen and there is no drift.

For AAIR pacing using the AV (or AR) interval as the control parameter, the software of FIG. 7 is modified to leave out any steps involving $V_{stim}$. Thus, elements 42, 55 and 63, and the "yes" paths branching therefrom, are not utilized. AV time intervals are obtained by using the far field sensing as discussed above and, of course, the source of the interval data has no effect on the software operation.

We claim:

1. A pacing system for rate responsive pacing of a patient's atrium, comprising:
   atrial generator means for generating and delivering atrial stimulus pulses at a variable atrial rate, to evoke atrial beats;
   senor means for sensing for field ventricular beats responsive to evoked atrial beats, said sensor means comprising an electrode adapted to be positioned in the patient's atrium;
   means for setting a reference value corresponding to the AV time delay between an atrial event and a following sensed ventricular event in the patient;
   means for determining the AV interval in said patient;
   algorithm means for (a) comparing said AV interval to said AV reference value, (b) for determining a change in the atrial pacing interval as a first function of said comparison, and (c) for adjusting said AV reference value as a second function of said comparison; and
   means for adjusting said atrial rate in response to said determined change.

2. The pacing system as described in claim 1, said system further comprising means for delivering ventricular beats to the patient's ventricle in the absence of a sensed ventricular beat and means for incrementing the atrial pacing interval following delivery of a ventricular stimulus.

3. The pacing system as described in claim 1, further comprising means for sensing natural atrial beats, means for determining when a predetermined pattern of natural atrial beats has occurred, and means for decrementing said AV reference value by a predetermined amount following determination of said natural atrial beat pattern.

4. The pacing system as described in claim 1, wherein said algorithm means is operative each cycle of said pacing system.

5. The pacing system as described in claim 4, wherein said algorithm means adjusts said reference value by a first predetermined increment and said change is a predetermined second increment of change in atrial pacing interval.

6. The pacing system as described in claim 5, wherein the first and second increments are each substantially constant for all atrial pacing rates.

7. The pacing system as described in claim 5, wherein said atrial generating means is rate adjustable throughout a predetermined range, and at least one of said first and second increments varies as a non-linear function of atrial rate.

8. The pacing system as described in claim 5, wherein said first and second increments are larger at lower atrial rates than at higher atrial rates.

9. A method of controlling the rate of delivering atrial stimulus pulses to a patient's atrium, using a pacing system having an atrial generator for delivering atrial stimulus pulses and an atrial lead with at least one electrode in said atrium, comprising
   sensing ventricular events from said atrial electrode;
   determining the AV time interval between said delivered atrial stimulus pulses and said sensed ventricular events; and
   adjusting atrial pacing rate as a function of said determined AV time interval.

10. The method of claim 9, wherein said adjusting comprises changing the interval between atrial stimulus pulses by a first programmed amount.

11. The method of claim 10, comprising calculating an AV reference value as a function of determined AV time interval.

12. The method of claim 11, comprising changing the value of said AV reference by a second programmed amount concurrent with each change of stimulus pulse intervals.

13. The method of claim 12, wherein each of said first and said second amounts is a programmable function of pacing interval.

14. A pacing system for rate responsive pacing of a patient's atrium, comprising
   atrial generator means for generating atrial stimulus signals at an adjustable rate;
   AV means for determining the AV time interval between an atrial event and a following ventricular beat;
   increment means for increasing or decreasing the atrial stimulus rate by a predetermined first increment as an adjustable function of said determined AV time interval;
   adjusting means for adjusting said adjustable function following each determination of AV time interval, said adjusting means comprising means for adjusting said AV reference value by a second increment following each AV time interval determination, and said increment means comprising means for comparing determined AV time interval with said AV reference value;

program means for programming at least one of said first and second increments; and lower limit means for further adjusting said AV reference when the determined AV time interval is greater than the AV reference at a predetermined lower rate limit.

15. A pacing system for AAIR pacing, having an atrial generator for generating atrial pacing pulses at a rate adjustable as a function of a control parameter, and an atrial lead for delivering said atrial pulses and sensing heartbeat signals, further characterized by signal processing means connected to receive said sensed heartbeat signals and for identifying R wave portions thereof corresponding to ventricular heartbeats, and timing means for timing the interval between a said atrial pulse and a following said R wave portion, thereby deriving the said control parameter.

16. The method of claim 9, further comprising sensing atrial events with said atrial lead, and wherein said AV time interval is the interval between atrial events and sensed ventricular events.

17. A pacing system for rate responsive pacing of a patient's atrium, comprising:

atrial generator means for generating and delivering atrial stimulus pulses at a variable atrial pacing rate, to evoke atrial beats;

sensor means for sensing ventricular beats responsive to evoked atrial beats;

AV means for determining AV interval between a delivered atrial stimulus pulse and a said sensed ventricular beat;

means for adjusting said atrial pacing rate as a function of said determined AV interval; and said system further comprising means for delivering a ventricular pace pulse to the patient's ventricle in the absence of a sensed ventricular beat following an atrial pace pulse and means for incrementing the atrial pacing interval following delivery of a said ventricular pace pulse.

18. The pacing system as described in claim 17, wherein said AV means comprises reference data means for storing AV reference data indicative of a predetermined curve of AV reference values as a function of pacing rate through a predetermined pacing rate range, and algorithm means for setting an AV reference value by determining from said stored AV reference data an AV reference value corresponding to the adjusted atrial pacing rate.

19. The system as described in claim 18, wherein said AV reference data represents a linear variation of said AV reference values with respect to pacing interval over said pacing range.

* * * * *

UNITED STATES PATENT AND TRADEMARK OFFICE
CERTIFICATE OF CORRECTION

PATENT NO. : 5,144,950

DATED : September 8, 1992

INVENTOR(S) : G.A.P. Stoop and Malcolm J.S. Begemann

It is certified that error appears in the above-identified patent and that said Letters Patent is hereby corrected as shown below:

In claim 1, col. 7, line 49, "for field" should read --far field--.

In claim 6, col. 8, line 19, delete "the" and substitute therefore --said--.

Signed and Sealed this

Fourteenth Day of September, 1993

Attest:

BRUCE LEHMAN

Attesting Officer     Commissioner of Patents and Trademarks